(12) United States Patent
Gergen, II

(10) Patent No.: US 12,295,877 B2
(45) Date of Patent: May 13, 2025

(54) MANDIBULAR ADVANCEMENT DEVICE AND METHOD

(71) Applicant: David Si Gergen, II, Peoria, IL (US)

(72) Inventor: David Si Gergen, II, Peoria, IL (US)

( * ) Notice: Subject to any disclaimer, the term of this patent is extended or adjusted under 35 U.S.C. 154(b) by 0 days.

(21) Appl. No.: 17/463,137

(22) Filed: Aug. 31, 2021

(65) Prior Publication Data

US 2023/0065574 A1   Mar. 2, 2023

(51) Int. Cl.
*A61F 5/56* (2006.01)

(52) U.S. Cl.
CPC ........ *A61F 5/566* (2013.01); *A61F 2005/563* (2013.01)

(58) Field of Classification Search
CPC ...... A61F 5/56; A61F 5/566; A61F 2005/563; A61C 7/08; A61C 7/36; A61C 7/282; A61C 19/04; A61C 19/045; A63B 2071/088
USPC ......................................... 128/848, 859, 861
See application file for complete search history.

(56) References Cited

U.S. PATENT DOCUMENTS

| | | | |
|---|---|---|---|
| 5,823,193 A * | 10/1998 | Singer | A61F 5/566 128/859 |
| 6,604,527 B1 | 8/2003 | Palmisano | |
| 10,898,369 B2 | 1/2021 | Farrell | |
| 2003/0198912 A1 * | 10/2003 | Mah | A61C 7/08 433/5 |
| 2011/0277774 A1 * | 11/2011 | Connell | A61F 5/566 128/848 |
| 2018/0161195 A1 * | 6/2018 | Carrillo Gonzalez | A61F 5/566 |
| 2020/0129270 A1 * | 4/2020 | Hofmann | A61F 5/566 |
| 2020/0323677 A1 | 10/2020 | Droter | |

FOREIGN PATENT DOCUMENTS

AU    2002100414 B4    11/2002

OTHER PUBLICATIONS

Braem M.J.A., et al., "Short-term results on a novel duo-block custom-made titratable mandibular advancement device using a flexible counter-balancing titration mechanism: a pilot study", American Academy of Dental Sleep Medicine, Abstract ID#9, AADSM Annual Meeting 2019.
Somnodent Avant brochure, SomnoMed's smallest, slimmest, strongest, and first milled oral device with a soft iner for the treatment of mild to moderate obstructive sleep apnea (OSA), SomnoDent Avant Study, Prof. Marc Braem, BE-UZA, Antwerp University Hospital, Aug. 2018.
Somnodent Avant brochure, Sleep Apnea Appliance, Copyright 2019 SomnoMed, Inc.

* cited by examiner

*Primary Examiner* — Keri J Nelson
*Assistant Examiner* — Daniel A Miller
(74) *Attorney, Agent, or Firm* — Bycer & Marion, PLC; Matthew L. Bycer

(57) ABSTRACT

A mandibular advancement device is disclosed. An upper component and a lower component are used as splints on the maxilla and mandible. A wire may be mounted to the lower components at the molar buccal sides. The wire passes through a channel on the anterior of the upper component, in a slidable fashion. The channel may be circular or have a cross-sectional shape including a flat side. A forward shield cushions or protects the interior of the oral cavity as the wire may move back and forth. The device may be made entirely of plastic or biocompatible materials.

21 Claims, 6 Drawing Sheets

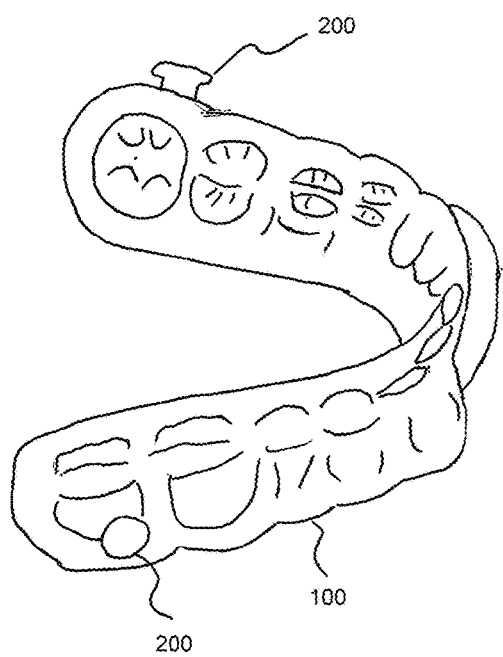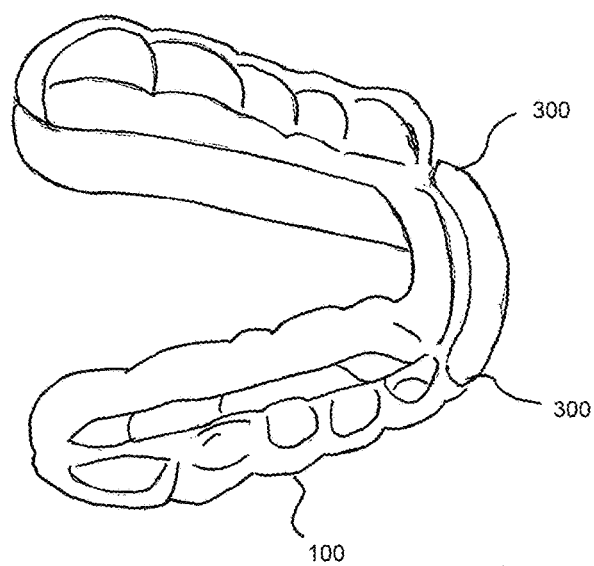
FIG. 8
FIG. 9

MANDIBULAR ADVANCEMENT DEVICE AND METHOD

BACKGROUND OF THE INVENTION

1. Field of the Invention

The present invention relates to an oral appliance for use in the treatment of sleep disorder breathing (SDB). The present invention more particularly relates to a mandibular advancement device that has application in the treatment of orthodontic conditions, snoring, obstructive sleep apnea (OSA) and certain temporomandibular joint disorders.

2. Description of Related Prior Art

Breathing disorders cause or contribute to a number of health problems. When resting, improper mouth alignment may lead to more severe disorders like Obstructive Sleep Apnea (OSA). OSA has been associated with the causes of heart disease, strokes and all as chronic daytime tiredness and spontaneous sleeping. Various forms of severity of OSA, snoring, and other syndromes have been described under the definition Sleep Disorder Breathing (SDB).

Snoring and sleep apnea are generally thought to be the result of a reduced or partial constriction of the airway during sleep. Soft tissues sink and apply pressure on the airway, which can be caused when the mandible drops and moves backwards.

Pathogenesis of OSA involves a combination of reduced upper airway size and altered upper airway muscle activity. These in turn cause oral tissue to collapse. Although muscles hold the pharyngeal airway open when awake, these muscles can relax when sleeping.

Snoring and OSA are caused by blockage of the pharyngeal airway by, for example, excess tissue when various muscles of the body, including the tongue, relax. As the tongue relaxes, it moves posteriorly, blocking the pharyngeal airway. When the pharyngeal airway is blocked, exhaled air is forced through the airway with increased velocity thereby causing vibration of the tongue, tissue, or other obstruction, thereby creating noise.

There are many types of Dental Sleep Appliances (DSA) used to treat these conditions. Mandibular advancement devices (MAD) are designed to move the mandible forward so as to relieve the force applied from soft tissue during sleep. MAD advance the mandible anteriorly relative to the maxilla, so as to open the pharyngeal airway by indirectly urging the tongue forward, to stimulate activity of the muscles in the tongue to increase the forward rigidity of the tongue. Since the tongue attaches to the posterior portion of the mandibular symphysis, advancing the mandible forward relative to the maxilla also pulls the tongue forward, thus preventing the tongue from obstructing the pharyngeal airway. MAD function to move the mandible, and hence the tongue forward to open the oropharynx.

The temporomandibular joint (TMJ) is the joint that connects the mandible to the skull. The mandibular condyle is received within the superior synovial cavity The TMJ is flexible, allowing the mandible to move smoothly up and down and side to side and enabling a person to talk, chew and yawn. Muscles attached to and surrounding the TMJ control the position and movement of the mandible. Continued use of devices that restrict the natural lateral movements as well as anterior and posterior movement of the mandible can potentially aggravate the TMJ and the related facial musculature.

Still further, mandibular advancement will clearly place stress on the TMJ as the mandibular condyle is anteriorly displaced relative to its normal position. TMJ disorder covers a group of conditions that cause pain and dysfunction in the jaw joint and the muscles that control jaw movement. Patients with existing TMJ disorders are generally cautioned against using MAD, as such devices can exacerbate the condition.

It is well established that the use of intraoral appliances for SDB therapy is an ongoing process.

One type of MAD is a single piece double mouth guard like device that fits to the upper and lower teeth. It is considered important that these devices allow essentially unrestricted breathing through the mouth. Other MAD devices are in two parts that are hingedly connected. Others are formed from a single piece of thermoplastic with a living Herbst Hinge. In 1909, Dr. Emil Herbst designed an orthodontic appliance to solve overbites.

To overcome skeletal discrepancies, mainly in young patients, the Herbst device has been used to influence efficient growth of the related anatomy. Many Herbst devices today are cemented directly on the teeth. Telescoping Herbst appliances allow for free-sliding of the jaw, while connecting the maxilla to the mandible via two tubes and a ball-and-socket joint with a rod attached to the mandibular premolars or cantilever arms.

The use of Herbst Hinges, or other metallic components can also cause problems for those with sensitivities to metal, especially when present and in contact with mucosal membranes through the mouth.

A recognized advantage of the hinged devices is that they allow the mouth to open for unrestricted breathing.

Currently, the criteria a custom-made oral appliance for OSA must meet to be Pricing Data and Analysis Coding (PDAC) approved for E0486 that is to be used to reduce upper airway collapsibility is as follows:

Have a fixed mechanical hinge at the sides, front, or palate;

Have a mechanism that allows the mandible to be advanced in increments of one millimeter or less;

Be able to protrude the mandible beyond the front teeth at maximum protrusion;

Be adjustable by the beneficiary in increments of one millimeter or less;

Retain the adjustment setting when removed;

Maintain mouth position during sleep so as to prevent dislodging the device.

However, prior art MAD pose potentially damaging effects. Most single piece devices fit over both the maxillary and mandibular teeth and are typically held stationary, thereby restricting movement, causing discomfort, and potential permanent repositioning of the jaw. Patients who grind their teeth, or otherwise require adjustment, will be harmed by a stationary device that may lead to cramping, choking, and other hazards.

A need exists to provide a mandibular advancement device that provides advancement of the lower jaw without unduly limiting movement of the jaw, and allows for relaxation of the muscles associated with the TMJ. Further a need exists for oral appliances that do not contain metal or other irritating substances that can react with some or all patients.

It is therefore a primary object of the present invention to provide an oral device that provides for treatment of breathing disorders.

It is another object of the present invention to provide a mandibular placement support device.

It is yet another object of the present invention to foster proper alignment of the maxilla relative the mandible.

It is as yet a further object of the present invention to provide a method for controlling location of the mandible.

It is a further object of the present invention to provide a method for creating an oral device.

These and other objects of the present invention will become apparent to those skilled in the art as the description thereof proceeds.

SUMMARY OF THE INVENTION

The present invention is directed to an oral device adapted to be inserted into the oral cavity. The present invention may take the form of an advancement device for the treatment of the oral anatomy. A lower component is adapted to mate or mount in a releasable fashion to at least a portion of the lower jaw, such as over the lower teeth or alveolar ridge. An upper component is similarly formed and adapted to mate in a releasably fashion with at least a portion of the upper jaw, such as an upper mouth guard over teeth/ridges. Upper and lower components may be adapted to mate with an intervening structure, such as an orthodontic aligner, retainer, clear final retainer, removable partial dentures, crown, denture, or other type of oral anatomy present in the patient, etc. Preferably, the upper and lower components are custom designed for any patient's unique current state of dentition.

A mounting point is set on the lower component, on either or both the left or right side, towards the molars, preferably on the buccal side of the device. A channel may be formed in the upper component, preferably through a portion of the anterior buccal side. A wire is coupled to the mounting point(s), preferably in a hinged fashion, the wire then passes through the channel and may mount on the opposite side of the lower component.

The wire may form a loop at the end of the wire. The loop may set around the mounting point, preferably around a post or boss emanating and extending from the buccal side of the lower component. The wire may be held in place by a radially extending mushroom shaped head. The wire passes into the channel through left and right apertures. The apertures are preferably anterior of the lateral incisors (or lateral of the lateral incisors when incisors are absent), and most preferably lateral of the lateral incisors. The channel forms a convex angle to match or align with the lateral arch of the maxilla, and may also include minor concave curve(s) towards the aperture(s).

The channel is preferably set within a forward shield that has bumpers fore, aft, above and below the channel. The channel may form a generally round cross-sectional shape, and may include one or more flat sides, preferably along the anterior edge of the channel.

BRIEF DESCRIPTION OF THE DRAWINGS

The present invention will be described with greater specificity and clarity with reference to the following drawings, in which:

FIG. 8 illustrates a right elevated perspective view of a lower component of an embodiment of the present invention.

FIG. 9 illustrates a right elevated perspective view of an upper component of an embodiment of the present invention.

DETAILED DESCRIPTION OF THE PREFERRED EMBODIMENTS

Figure 1:
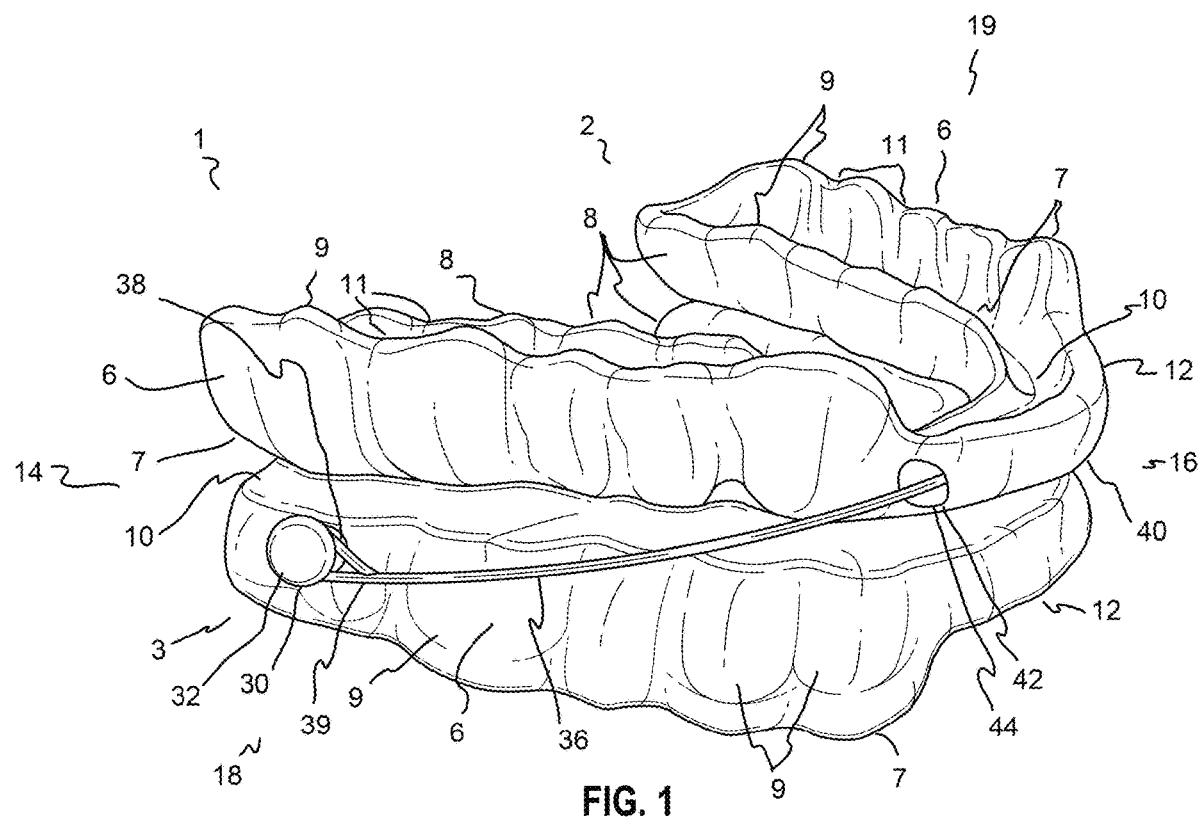
FIG. 1 illustrates a right elevated perspective view of a joined two-piece mouth guard embodiment of the present invention.

Due the advancements in product design and development technology, particularly with the use of additive printing of three-dimensional objects, it has become possible to print negative spaces (or empty voids) within a product. This allowed for the creating of a void channel in the front of an oral appliance that could be used to house or contain a wire slidable run therethrough. While additive printing is preferred, the current product may be handmade, or molded, wherein the channel is drilled through the front face of the maxillary component body. The preferred diameter size of the channel should be at least twice the diameter of the wire. This allows for the wire to be doubled over to pass through with a loop pre-attached. However, where the wire is formed with the device, the channel may be at or slightly larger in diameter than the wire.

With use of embodiments of the present invention, one may provide for mandibular advancement relative the maxillary structures and skull. The present invention maybe used to prevent adverse deformation of the tissues and bones associated with the mouth, or to correct misplacement and malalignment issues. Most commonly, the product may be used as a support to maintain the relative position of the mandible to the maxilla during sleep to prevent collapse of the soft tissues leading to SDB.

It is contemplated that the device may be comprised of two components, an upper component adapted to mate or otherwise couple with the upper maxilla. A second lower component may be adapted to couple or mate with the lower mandible. Both upper and lower components are preferably joined by a wire, most preferably a single wire, joined at two ends to the lower component and passing through an anterior section of the upper component. In alternative embodiments, a single mouthpiece unit containing both a maxilla and mandibular mounting surface, or coupling shape, may be used. Features on one or both of the upper or lower component may be adapted to mate with any dentition including a further mouth guard, an orthodontic aligner, dentures, standard natural teeth, implants, or even an edentulous mouth and oral cavity surfaces. The body structure of the upper and lower splints/components is preferably custom designed in digital software to create a path of insertion over any type of detention or device that a patient may currently use to assist in treatment of snoring and obstructive sleep apnea.

To avoid metal allergies, the device is preferably free of metals, including the wire, hinges, bolts/bosses, etc. The device is preferred to be self-ligating on the lower jaw, while maintaining loose balance on the orthodontic arch and U-shape function. Preferably, the device will not impede on the lip. A forward shield may blend the contours of the device to shield the lip while obtaining maximum natural comfort for increased patient compliance. As there are significant rules and regulations involved in oral appliance, the present invention is preferably compliant with U.S. regulatory, American Dental Association (ADA) guidelines, and various insurance carriers/companies for the provision of computer-aided design/computer-aided manufacture (CAD/CAM) metal-free devices.

It is preferred that the wire(s) move freely through the channel and are self-ligating. This is intended to allow the lower jaw to naturally nestle on the skull in a most comfortable manner possible. As every patient has a different anatomy, with their jaws opening and closing off- or near-perfectly on the Right or Left side, many patients' jaws, especially TMJ cases where their jaw opens or naturally pulls to one side or the other, will not close perfectly even or straight. The device should allow for a slight slack to one side or the other, with the wire passing laterally through the channel. Preferably, this avoids issues with activating both sides of a device to find a sweet spot. The present device is intended to allow the patient to comfortably swing their mandible (like a hammock) into position/balance.

Three-dimensional or additive printers are preferred to utilize materials as are known in the art compatible with such printing. For example, nylons, including Nylon12, and the like, may provide a good material for the components. More optimum Nylon or polyamide synthetic polymers are also useful. Acrylics and Dental Splint Resin and polymers are also preferred. Characteristics of strength, stain resistance, odor and bio resistance, anti-microbial and non-porous materials, are preferred. Materials preferably include strength characteristics to avoid breakage up to or more than 50 MPa, tensile modulus above 1,000 MPa, with a flexural strength of 50+ MPa, and flexural modulus of 1,000 MPa or more. Shore D hardness may begin at 30D (or 20D for EVA use), and is preferably up to 70D, or more preferably 80-90D akin to alignment orthodontics.

The materials are preferably designed to be long term use in the patient's mouth to resist stain, hold strength from bruxism, and retain shape over long term to survive wear-and-tear. The component body thickness preferably varies between 2-3 mm thick, with smaller adult mouths maybe using 2 mm thick walls, while larger mouths may be buttressed with more material thickness for more durability. On the buccal and lingual sides, the preferred thickness in the upper anterior is 2-3 mm thick to create space for the channel in a forward shield. The thickness on the occlusion or engaging surfaces (bottom of upper and top of lower component) where the two splints touch within the oral cavity, is preferably a thicker 4-5 mm thick. Selection will depend on the patient's Curve of Spee (curvature of the mandibular occlusal plane beginning at the premolar and following the buccal cusps of the posterior teeth, continuing to the terminal molar). As some patients have deep bite or open bites, thickness may vary within and between devices.

The wire is preferably made of a clear fluorocarbon, similar to fishing wire, and/or nylon. Transparency or translucence is not necessary for the device to work. The wire can also be 3D-printed in Nylon. The wire may be circular in cross-section flattened, or a tape (with severely thin rectangular or oval cross-section. The wire channel is preferably less than 3 mm in diameter.

As shown in FIG. 1, device 1 includes upper component 2 and lower component 3.

Upper component 2 and lower component 3 are joined via wire 36. Viewed from the right side 18, mounting point 30 (or points) is set on lower component 3 towards second or third lower molar. It is contemplated that a complementary mounting point will be similarly situated on the left side (shown in FIG. 2). Mounting point 30 preferably includes an extending boss or bolt that includes a neck 34 with a wider head 32 set thereon, head 32 having a wider diameter than neck 34 in order to entrap or otherwise secure wire loop 38 thereon. In most preferred embodiments, a single wire 36 is looped at both ends with loops 38 that pass over and reconnect at tie points 39. Mounting point 30 may include a singularly molded, or printed feature that is unitary with lower component, or may be a flat or round headed screw or bolt or other fastener as is known in the art, that may be drilled or otherwise fastened into buccal wall 6 of the lower component.

Preferably, the point or distal tip of the fastener opposite the head does not pass through the entirety of the buccal wall 6 so as not to interfere with the teeth or other apparatus or dentition set thereon. Most preferably, mounting point, and all features of the device, will be made of a nonreactive or inert substance, such as an organic material, synthetic or semi-synthetic polymer or plastic, or the like. While metal bolts and mounting points are commonly used in the art, it is preferred to avoid any use of inorganic metals that may cause an allergic or irritation to the oral cavity surfaces of sensitive users. Therefore a unitary body construction wherein the mounting point is of the same material as the upper and lower components is preferred. The upper and lower components may be made of alternative materials, and most preferably of the same material. The upper and lower components may be extruded, pressed, molded, additive printing, or otherwise delivered as a thermoplastic boil and bite material such as an ethylene vinyl acetate (EVA). Custom-made components are preferred, and may be designed using three-dimensional imaging to create a digital impression of the oral cavity and dentition surfaces, or another apparatus upon which the components will be mounted.

Upper component 2 includes buccal walls 6 fitting around a perimeter, and lingual walls along an interior perimeter of the upper component 2. Lingual walls 8, and more pronounced on buccal walls 6, teeth bulges 9 may include both outwardly extending bulges as well as risers along the tooth or other dentitious surfaces. Altogether, contours 7 should match with the preferred dentition so as to complement features upon which the upper component shall be mounted. Between teeth bulges 9, teeth gap recesses 11 may be set as thicker or thinner portions of the buccal and lingual walls. Device 1 has a molar or posterior 14 side as well as an anterior 16. An anterior recess 12 is preferably set towards anterior 16 and includes a dip that exposes a portion of or portions of central incisors, and more preferably extends partially or completely laterally past the lateral incisors. An engaging surface 10 is set along the lower edge of the dentition (and at an upper edge for the lower component as described below). Anterior recess may include a slight dip, depending on the length of the teeth, to ease the path of inserting the device into the oral cavity (as incisors are often much more sensitive than posterior teeth).

Wire 36 is preferably rotatably engaged to mounting point 30 to allow for upper component 2 and lower component 3 to separate vertically and horizontally when device is in use. Users who grind their teeth or otherwise open and close their mouths may require or prefer a tie that slides and rotates along mounting point. Wire 36 passes through a channel 42 set along and within forward shield 40 at anterior 16 of upper component 2. Channel preferably passes through a right entry 44 and a left entry (shown below) and again mounts to a further mounting point on left side (shown below). Wire preferably passes through channel 42 in a slidable fashion that may or may not include contact with interior surfaces of channel 42. It is preferred that the channel at least include an enclosed portion wherein the wire is ligated within.

Lower component 3 also includes buccal walls 6 and lingual walls (not shown in FIG. 1). Lower component 3 includes contours 7, teeth bulges 9, and engaging surfaces 10. A further anterior recess 12 may also be set on lower component 3 preferably along the central and lateral incisors. While an anterior recess 12 is shown in both upper and lower components, the anterior recess is not required for this device to work.

Figure 2:
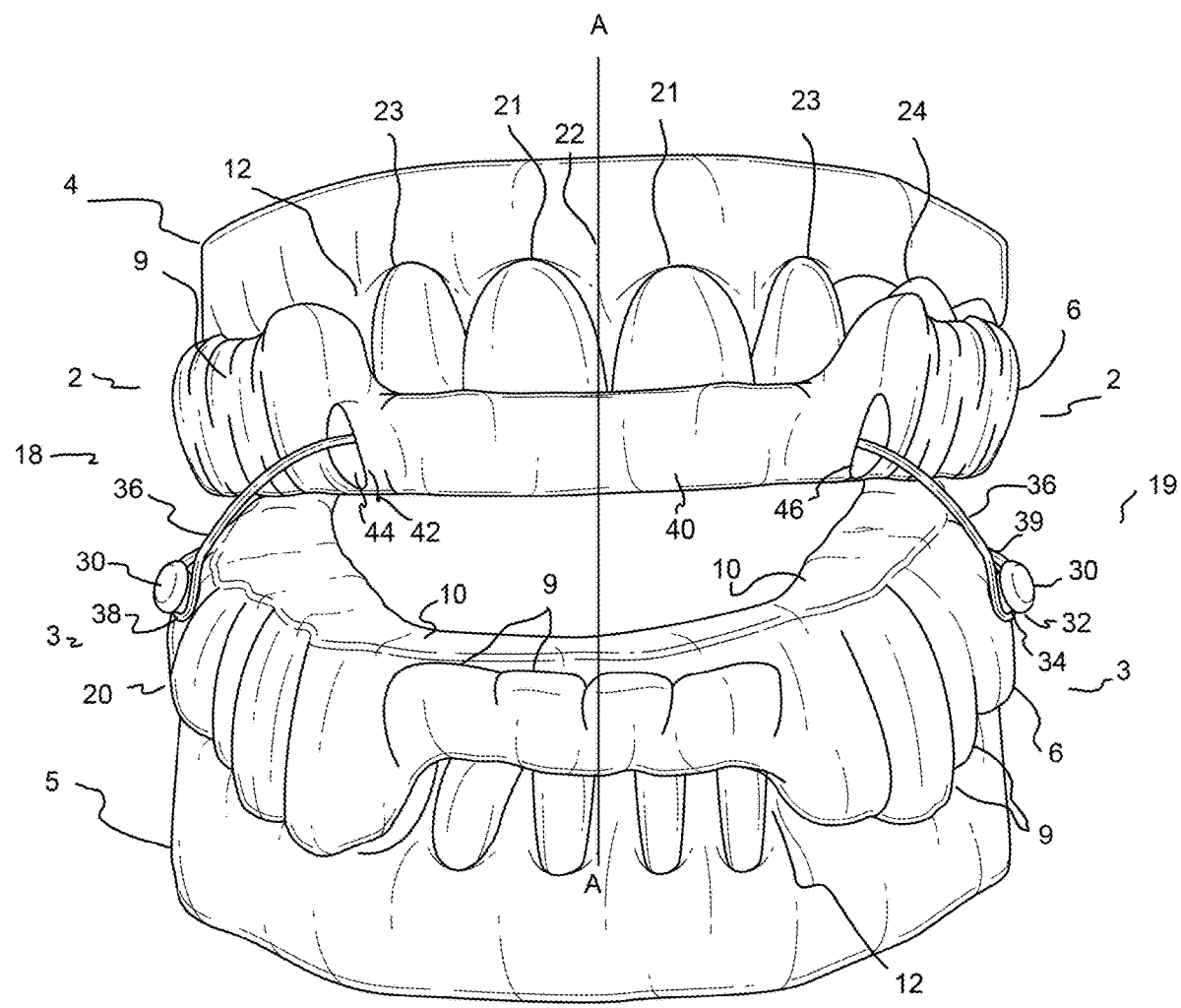
FIG. 2 illustrates a frontal view an embodiment of the present invention applied to a full dental anatomy.

Referring to FIG. 2, a front view of the device 1 with upper component 2 and lower component 3 applied to a denture or teeth of a user. Upper jaw 4 (maxilla) includes central incisors 21, lateral incisors 23, and a midline 22. Shown here is an exemplary dentition, however, as it is known in the art, various oral cavities and users have a variety of mouth structures. For demonstration purposes, a dentition with both central incisors and both lateral incisors is shown. The location of the right entry 44 and left entry 46 of channel 42 within forward shield 40 is shown. Preferably, right and left entries, 44 and 46, are set forward or anterior of the lateral incisors 23, or more preferably outside and wider than the lateral incisors. Similarly, anterior recess may dip below central and lateral incisors, may be limited to the central incisors or may be absent entirely. Upper component 2 is shown with buccal walls 6 having teeth bulges 9 associated with dentition shown. Lower component 3 is set on lower jaw 5 (mandible). Lower component 3 includes teeth bulges 9 associated with dentition as shown. Engaging surface 10 is shown. Engaging surface 10 serves to allow upper and lower components to easily slide against one another. Engaging surface is preferably more flat than the actual teeth or other dentition surfaces to allow for a smoother slide against one another as may be comfortable or more ergonomic for the user. In some embodiments, upper and lower engaging surfaces may have complementary features so as to limit horizontal movement, both lateral and anterior posterior and otherwise engage the maxilla and mandible in a set position. Wire 36 spans from left side 19 to right side 18 mounting at mounting points 30 held in place via heads 32 with loops 38 set around neck 34 of mounting point 30. Preferably, wires are tied at tie points 39 to the wire, otherwise the wire may include a fixed loop that is otherwise affixed to ends of the wire (not shown). Mounting points are set along second, and more preferably third molar position on the mandible. A central midline is denoted by vertical line AA and serves as the indication for the cross-section shown in FIGS. 3 and 4 below.

Figure 3:
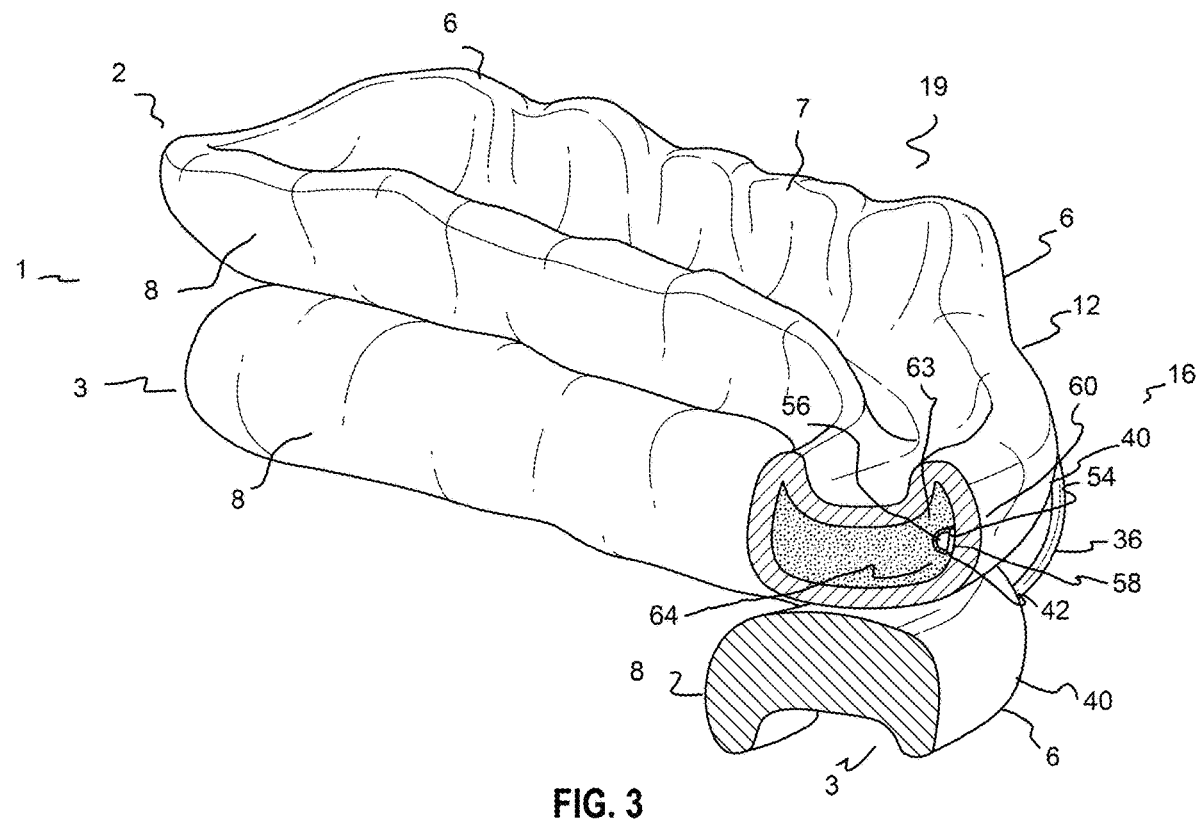
FIG. 3 illustrates a right elevated perspective cross-sectional view of one embodiment of the mouth guard as shown in FIG. 2 along the line 3-3.

As shown in FIG. 3, a preferred left section on left side 19 is shown of device 1, including both upper component 2 and lower component 3. As shown, lingual walls 8 are set on the interior of device while buccal walls 6 are set on the outside perimeter. Contours 7 are shown to demonstrate a complementary feature of the device to mate and allow mounting onto any dentition or other device. Along anterior 16, anterior recess 12 is shown along an anterior side of device. Forward shield is shown on both upper component 2 and lower component 3. Forward shield is preferably rounded and sleek so as to avoid irritation on the interior surfaces of the oral cavity, e.g. lips, cheeks, etc. Wire 36 extends from lower component 3 into channel 42 (entry on left not shown). Device components may be a single solid material, or may otherwise include an exterior shell 50 with interior 52. One, two, or more materials may be used to build the components, including a separate shell material that may be harder and more slippery than interior material.

Forward shield 40 on upper component 2 preferably includes in channel 42 set with an anterior spacing 60 that acts as a bumper on the anterior side of the device. A rear bumper 63 and lower bumper 64 may be similarly situated around channel 42 to provide protection to oral cavity surfaces, or other appliance surfaces, so as to avoid rubbing wire against features of the mouth that may otherwise cause irritation. It is contemplated that the wire may move freely through the channel back and forth as may be required when using the device. Channel 42 preferably includes channel walls 54 which may or may not be reinforced so as to maintain the integrity of the channel. Channel 42 further includes channel space 56 wherein a cross-section of the channel delineated via channel walls may form a special shape. In some embodiments, such as shown in FIG. 3, a flat wall 58 may be set to define the shape of the channel. Flat wall is shown on the anterior side so as to limit any bulging on the anterior side of forward shield 40. Alternatively, a flat wall or additional flat wall may be set on the posterior side of channel.

Figure 4:
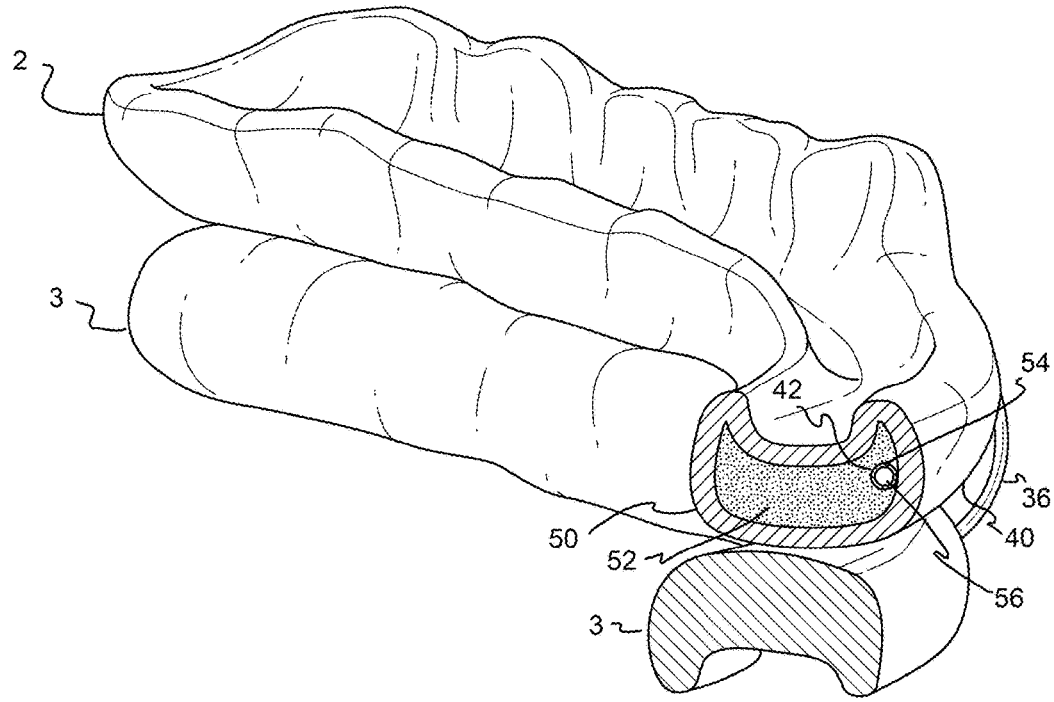
FIG. 4 illustrates a right elevated perspective cross-sectional view of an alternative embodiment of the mouth guard as shown in FIG. 2 along the line 3-3.

As shown in FIG. 4, upper and lower components may include a solid (lower component 3) or dual natured (as shown on upper component 2) materials with outer shell 50 and interior 52. In this embodiment, channel 42 is shown with a round cross-section including channel walls 54 and interior 53. Channel 42 is set within forward shield 40 and allows for wire 36 to pass therethrough. While a round cross-section may be preferred, according to this description, deviations from a perfectly circular cross-section may occur and may be preferable in this invention. For purposes of this disclosure, a cross-section or shape may be generally circular if it does not deviate more than ten percent in either angle or shape dimension from an idealized circle or other shape. Further, a flat wall may extend vertically, or generally vertically if within a 15-degree deviation from vertical.

Figure 5:
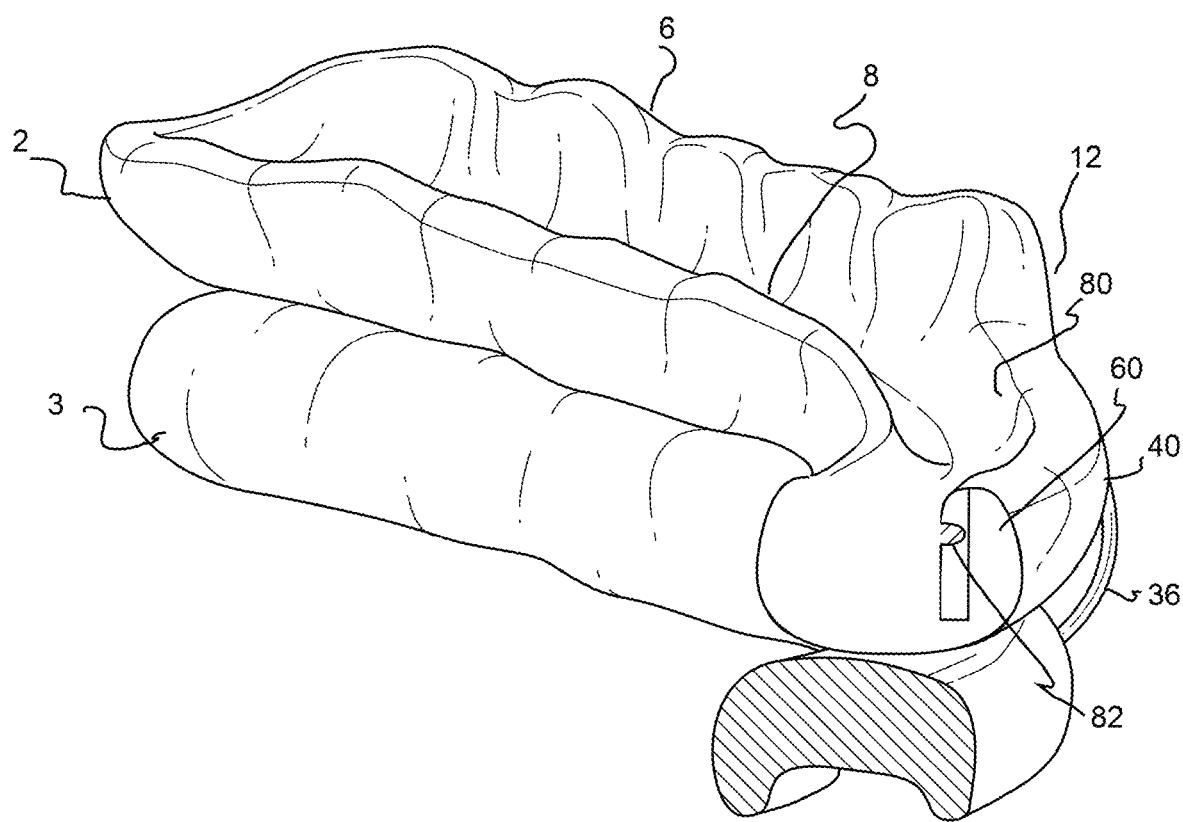
FIG. 5 illustrates a right elevated perspective cross-sectional view of an alternative embodiment of the mouth guard as shown in FIG. 2 along the line 3-3.

To accommodate items mounted onto the anterior edge of teeth, such as a brace or ornament, certain structures or indents may be formed on the interior side of the buccal wall, as shown in FIG. 5. When a user wishes to place the device directly on their natural dentition, but the dentition includes artificially adhered bulk, such as braces or ornaments (e.g., gems), upper component 2 may include indents 82 formed into buccal wall 6 interior surface 80. Indents 82 may take the form of a semicircular dome, general negative space, formed to shape of bulk, and/or may include a bar to accommodate bulk on and between various teeth (e.g., braces joined by wire). Indent 82 forms into buccal wall 6 and enters into forward shield 40 impacted anterior bumper, indent preferably above channel (not shown).

Figure 6:
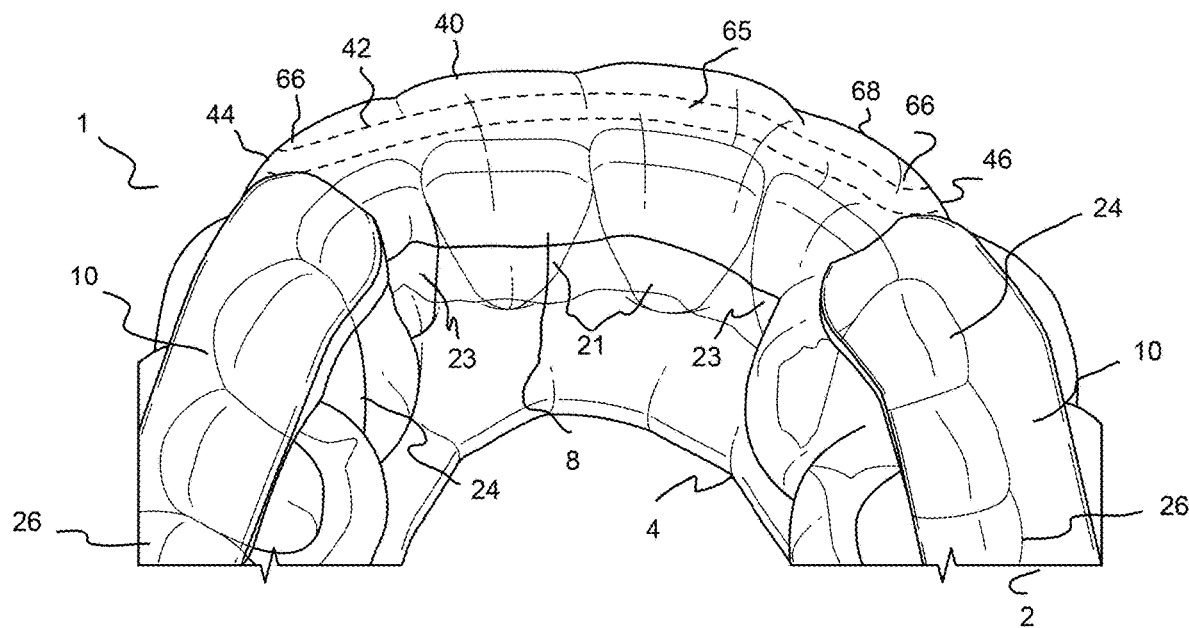
FIG. 6 illustrates a partially transparent bottom view of an upper component affixed to a maxilla dental anatomy of an embodiment of the present invention.

As shown in FIG. 6, a bottom view of upper component 2 mounted onto a typical dentition illustrates location of upper component and channel 42 relative to a common maxillar dentition. Upper component 2 is mounted onto upper jaw 4. Lingual walls 8 are shown on an interior perimeter. Maxilla 4 includes central incisors 21, lateral incisors 23, canines 24, and molars, including second molar 26. It is preferred that the mounting points will be set opposite second molars or more preferably third molars on lower component (not shown here). Channel 42 is set within forward shield 40 as shown. Channel 42 stands between right entry 44 and left entry 46 to allow for wire (not shown) to pass therethrough unobstructed. As shown, it is preferred that right and left entries 44 and 46 are set lateral or outside of the lateral incisors 23. The channel is enclosed to ligate, or capture the wire, and ensure it only enters/exits the right/left apertures. In some embodiments, it is preferred that the right and left entry be set anterior of the lateral incisors, or most preferably lateral and anterior of the lateral incisors 23. It is preferred that the channel be enclosed at least 4 mm, and more preferably at least 8 mm, and most preferably, entirely as between the apertures set lateral of the lateral incisors (approximately 15-30 mm, depending on patient anatomy). In order to match the shape of the maxilla, and otherwise to provide for an ergonomic and unobstructed shape, channel may be formed with a major arc 65 stretching anteriorly between right and left entries. Further, it is preferred in some embodiments that channel 42 includes minor arc 66 at one or both of the lateral sides towards the entries. Minor arcs serve to cause a near perpendicular mating surface with the outer surface 68 of upper component 2. Engaging surfaces 10 may be set flat and below tooth structures.

Figure 7:
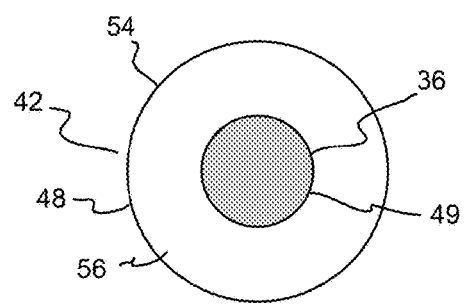
FIG. 7 illustrates a cross-sectional view of a channel of an embodiment of the present invention.

As shown in FIG. 7, a cross-section of an idealized round channel is shown. Wire 36 shown in cross-section includes a set diameter 49. Channel 42 includes channel walls 54 defining a size or diameter 48 for channel 42. A hollow channel space 56 is set therein. Preferably, channel diameter 48 is at least twice that of wire diameter 49. The size of the channel may be set to ensure that the wire may be doubled over when in looped form to pass through channel. When wire will be affixed to alternative looping ends, such as the use of a separate item attached to wire ends, diameter of channel may be smaller. To ensure that wire when doubled over can fit through channel, it is more preferred that the channel diameter 48 exceeds two and one-half, or more preferably four times the diameter of wire 49. Wire is preferably made from a slick substance, preferably a perfluorocarbon material (PFC). The slick nature of PFC allows for the wire to slide easily through channel. As device is used, channel may be cleaned with standard pipe cleaners that are flexible enough to pass through minor and major arcs, or the device may be submerged entirely in a cleaning solution. Debris set within channel if not removed can interfere with the sliding and initial entry of wire, therefore the diameter of channel is preferred to be at least two and one-half times the diameter of wire. As the device is used, however, the channel may be worn and widened through various use, and the bumpers anterior, posterior, above and below, particularly the posterior and lower bumpers, serve to provide cushion and additional wear surface and volume to accommodate long term use of device.

Embodiments using a round wire passing through the channel acts as a freely passive self-ligating action. As each patient's jaws open and close uniquely, the device preferably allows the condyle to settle ergonomically, while being protruded. Bilaterally swinging or side-to-side movement is preferably uninterrupted due to the proper U-shape flow of the cordage, until the patients jaw relaxes and rests in their own comfort place for their condyles/TMJ joint. When wire is in a tape or flat form, the size of channel may be reduced dramatically. The flat portion may be set forward and the wire may be placed with a long dimension up/down Referring to FIGS. 8 and 9, the body 100 for each of the upper and lower components are preferably one solid unit each. Body 100 is preferably printed via additive printing technique and made of a Dental Splint Resin or Nylon Resin as are known in the art, and preferably being biocompatible materials. Similar to Herbst Hinge electronic design for anchorage, mounting points 200 may be set bilaterally opposite the molars, and are preferably a nub type of anchorage.

Tubing 300 is preferably subtracted from the forward shield on the anterior of upper component. Three-dimensional electronic tubing may be subtracted from the body-part to form a channel. The channel may be a full circular channel or may be a semicircle in shape. The channel includes two apertures, and entrance and exit point, the entrance and/or exit positioned from maxillary lateral to lateral incisors.

Cord or wire 400 mounts to hinge points and pass-through channels. Wire is preferably made of a fluorocarbon material and may be pre-fabricated in the figure of a straight line with two loops on the ends. Alternatively, the wire may be electronically printed with Nylon or other biocompatible material.

The present embodiments demonstrate a first Metal Free Medicare appliance for treatment. Cordage may come in unlimited sizes advancing in 1 mm increments. Every time doctor seeks to advance the lower jaw forward, the cordage may be removed and replaced with a new cord that is 1 mm longer or shorter, or in similar increments. All patient arch/teeth forms are different; therefore, it is preferred to electronically measure the bite registration to the distance from the patient's midline (the middle space between front two teeth) to the Herbst Hinge on the lower molars to determine how long the cordage needs to be for that patient. The doctor or care giver may be provided with multiple cordages up to 10 mm advancement in total or more.

The preferred anchor may be a cylinder shape with a dome-like fixture on top of it to prevent the loop or wire from sliding off the cylinder figure anchor point. The anchor point is preferably mechanical and should bear the two solid 3D printed dental components together with the cordage having limited movement and rotation to advance forward.

In all embodiments, the components may be a hard or soft solid, gel or otherwise material as known in the art for oral treatments, such as silicone, rubber, plastic, calcium, silver, zinc, or otherwise.

I claim:

1. An advancement device for the treatment of the oral anatomy, comprising:
   at least one lower component having an attachment structure that is adapted to be releasably attachable to at least a portion of the lower jaw, and a lateral buccal side; and
   at least one upper component having an attachment structure that is adapted to be releasably attachable to at least a portion of the upper jaw, and an anterior buccal side; and
   said at least one lower component comprising at least one of a left or right mounting boss extending from the lateral buccal side;
   said at least one upper component comprising an enclosed channel formed through a portion of said anterior buccal side;
   a wire hingedly coupled to said at least one of a left or right mounting boss, and passing through said enclosed channel, wherein said wire extends into a first aperture set on a first buccal lateral side and out a second aperture set on a second buccal lateral side wherein the enclosed channel comprises a middle anterior section adapted to be positioned anterior between lateral incisors and along an anterior buccal side of the upper component between the between the first aperture and the second aperture, wherein said enclosed channel is completely enclosed between the first and second apertures and said wire is set through said middle anterior section; and a forward shield adapted to be set within an anterior spacing on the anterior buccal side anterior of the maxillary alveolar ridge, positioned anterior of said enclosed channel.

2. The device as set forth in claim 1 wherein said at least one of a left or right mounting boss is set on a right side, said device further comprising a second boss opposite said at least one of a left or right mounting boss and on a left side.

3. The device as set forth in claim 2 wherein said wire comprises a first end and a second end, a first loop formed at the first end, said first loop set around said at least one of a left or right mounting boss, said wire passing into a first aperture into said enclosed channel and out of a second aperture out of said enclosed channel, and said second end mounted onto said second boss.

4. The device as set forth in claim 3 wherein said wire second end forms a second loop formed at said second end, said second loop formed around said second boss.

5. The device as set forth in claim 1 wherein said wire forms at least a first loop set around said at least one of a left or right mounting boss.

6. The device as set forth in claim 5 wherein said at least one of a left or right mounting boss comprises a protruding head.

7. The device as set forth in claim 1 wherein said upper component comprises a dual material including an interior of a first material and a shell of a second material.

8. The device as set forth in claim 7 wherein said enclosed channel forms a major convex anterior arch.

9. The device as set forth in claim 7 wherein said enclosed channel forms a concave arch proximate at least one of said first and/or second apertures.

10. The device as set forth in claim 7 wherein said first material comprises a thermoplastic boil such as ethylene vinyl acetate, and said second material comprises at least one of nylon, acrylic, and/or a polyamide synthetic polymer.

11. The device as set forth in claim 1 wherein said enclosed channel comprises a cross-section with a flat wall defining the shape of the channel.

12. The device as set forth in claim 11 wherein said flat wall is set on an anterior side of said enclosed channel.

13. The device as set forth in claim 1 wherein said at least one of a left or right mounting boss is adapted to be set opposite a $2^{nd}$ lower molar.

14. The device as set forth in claim 1 wherein said at least one of a left or right mounting boss is adapted to be set opposite a $3^{rd}$ lower molar.

15. The device as set forth in claim 1 wherein said upper and lower components and said at least one of a left or right mounting boss consist of plastic material.

16. The device as set forth in claim 15 wherein said wire comprises plastic.

17. The device as set forth in claim 1 wherein said enclosed channel forms a generally circular cross-sectional shape.

18. An oral device for the treatment of the oral anatomy, comprising:

at least one lower component having a lateral buccal side; and at least one upper component having an anterior buccal side; and said at least one lower component comprising at least one of a left or right mounting boss extending from the lateral buccal side;

said at least one upper component comprising an enclosed channel formed through a portion of said anterior buccal side with apertures on opposing ends of the enclosed channel;

a wire coupled to said at least one of a left or right mounting boss; said wire passing through said enclosed channel; and a forward shield adapted to be set within an anterior spacing on an anterior buccal side anterior of the maxillary alveolar ridge, positioned anterior of said enclosed channel.

19. The oral device as set forth in claim 18 wherein said forward shield is in direct contact with the enclosed channel.

20. The oral device as set forth in claim 19 wherein said forward shield is in direct contact with an exterior shell of said at least one upper component.

21. The oral device as set forth in claim 18 wherein said forward shield is located within an interior material of said at least one upper component.

* * * * *